United States Patent
Lee et al.

(10) Patent No.: US 9,597,052 B2
(45) Date of Patent: Mar. 21, 2017

(54) METHOD AND APPARATUS FOR STORING X-RAY DATA IN X-RAY DETECTION MODULE

(71) Applicant: SAMSUNG ELECTRONICS CO., LTD., Suwon-si (KR)

(72) Inventors: Sang-min Lee, Suwon-si (KR); Sung-kyu Park, Uiwang-si (KR); Min-kook Cho, Hwaseong-si (KR); Ji-hoon Kang, Hwaseong-si (KR); Jin-hwan Oh, Suwon-si (KR); Jerome Crocco, Braga (PT)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 290 days.

(21) Appl. No.: 14/314,775

(22) Filed: Jun. 25, 2014

(65) Prior Publication Data

US 2015/0182184 A1    Jul. 2, 2015

(30) Foreign Application Priority Data

Dec. 26, 2013 (KR) .......................... 10-2013-0164130

(51) Int. Cl.
A61B 6/00 (2006.01)

(52) U.S. Cl.
CPC ............ *A61B 6/563* (2013.01); *A61B 6/4233* (2013.01); *A61B 6/488* (2013.01); *A61B 6/544* (2013.01); *A61B 6/566* (2013.01)

(58) Field of Classification Search
CPC ..... A61B 6/032; A61B 6/5205; A61B 6/4266; A61B 6/52
See application file for complete search history.

(56) References Cited

U.S. PATENT DOCUMENTS

| 4,815,118 A | 3/1989 | Acharya |
| 5,629,524 A | 5/1997 | Stettner et al. |
| 6,891,476 B2 | 5/2005 | Kitaguchi et al. |
| 2011/0157418 A1* | 6/2011 | Raynor ............... H04N 5/3415 348/229.1 |
| 2012/0193545 A1 | 8/2012 | Tkaczyk et al. |

FOREIGN PATENT DOCUMENTS

| EP | 2469305 A2 | 6/2012 |
| JP | 2002365366 A | 12/2002 |
| JP | 200658220 A | 3/2006 |

OTHER PUBLICATIONS

Communication dated Jan. 21, 2016, issued by the Korean Intellectual Property Office in counterpart Korean Application No. 10-2013-0164130.
Communication dated Nov. 17, 2015, issued by the Korean Intellectual Property Office in counterpart Korean Application No. 10-2013-0164130.
Communication dated Mar. 17, 2015, issued by the Korean Intellectual Property Office in counterpart Korean Application No. 10-2013-0164130.
Communication dated Jun. 1, 2015, issued by the European Patent Office in counterpart European Application No. 14193506.4.

* cited by examiner

*Primary Examiner* — Hoon Song
(74) *Attorney, Agent, or Firm* — Sughrue Mion, PLLC

(57) ABSTRACT

A method for storing X-ray data includes acquiring the X-ray data by using an X-ray detection module; and transmitting all or some of the acquired X-ray data to other X-ray detection module which is different from the X-ray detection module that has acquired the X-ray data.

18 Claims, 9 Drawing Sheets

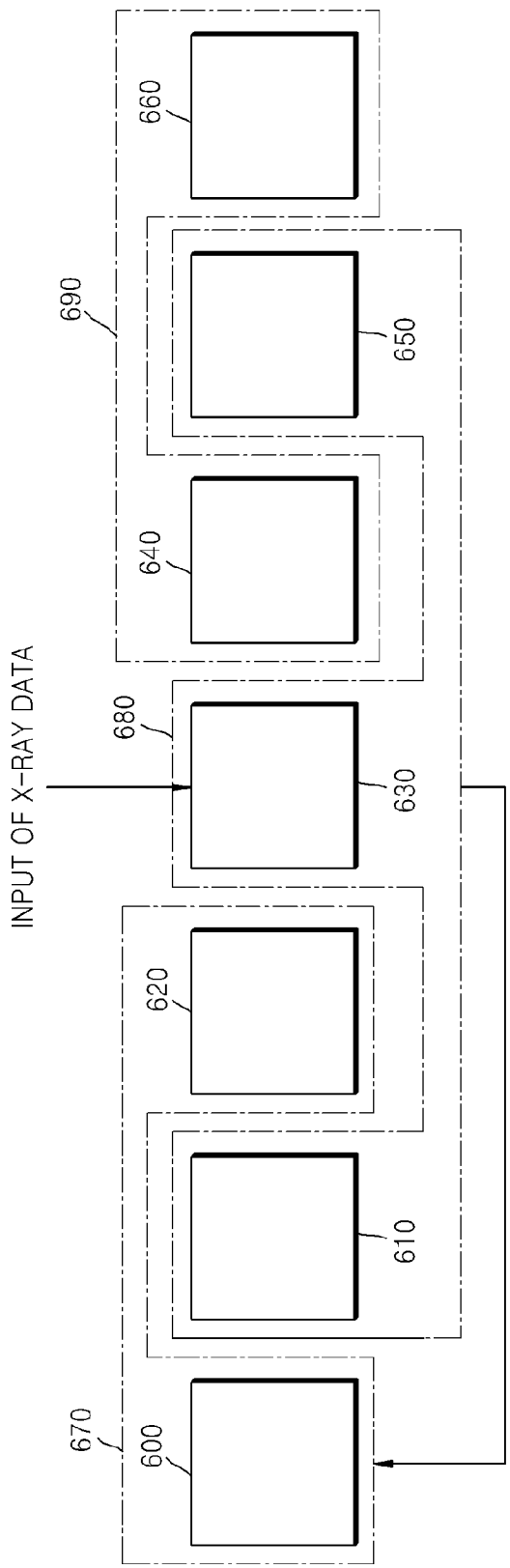

METHOD AND APPARATUS FOR STORING X-RAY DATA IN X-RAY DETECTION MODULE

CROSS-REFERENCE TO RELATED APPLICATION

This application claims priority from Korean Patent Application No. 10-2013-0164130, filed on Dec. 26, 2013, in the Korean Intellectual Property Office, the disclosure of which is incorporated herein in its entirety by reference.

BACKGROUND

1. Field

Apparatuses and methods consistent with exemplary embodiments relate to storing X-ray data in at least one X-ray detection module including a storage device.

2. Description of the Related Art

An X-ray apparatus acquires images of internal structures of the human body by transmitting an X-ray through the human body. The X-ray apparatus may acquire medical images of an object within a shorter time than other medical imaging apparatuses such as an MRI apparatus and a CT apparatus. Therefore, the X-ray system is widely used in a chest imaging, abdomen imaging, skeleton imaging, nasal imaging, neck soft tissue imaging, and breast imaging.

X-ray detectors, which detect radiation having passed through the object, may include a plurality of X-ray detection modules. Each of the X-ray detection modules receives X-ray data, and transmits the X-ray data to a storage device that is provided outside a corresponding X-ray detector.

SUMMARY

One or more exemplary embodiments include a method and apparatus for storing X-ray data in at least one X-ray detection module.

One or more exemplary embodiments include a method and apparatus for distributing all or some of X-ray data of an object, acquired from at least one of a plurality of mutually communicable X-ray detection modules, to the plurality of X-ray detection modules.

According to one or more exemplary embodiments, there is provided a method of storing all or some of X-ray data of an object, acquired from at least one of a plurality of mutually communicable X-ray detection modules, in the plurality of X-ray detection modules.

According to one or more exemplary embodiments, a method of storing all or some of X-ray data of an object, acquired from at least one of a plurality of mutually communicable X-ray detection modules, in the plurality of X-ray detection modules, includes: acquiring the X-ray data by using an X-ray detection module; and transmitting all or some of the acquired X-ray data to at least one other X-ray detection module other than the X-ray detection module.

The method may further include activating at least one of the plurality of X-ray detection modules, wherein, the acquiring may include acquiring the X-ray data by using the activated X-ray detection module, and the transmitting may include transmitting all or some of the acquired X-ray data to at least one other X-ray detection module other than the activated X-ray detection module.

The activating may include activating at least one X-ray detection module included in a predetermined X-ray-detectable range among the plurality of X-ray detection modules depending on a size of the object.

The activating may include storing the acquired X-ray data in a storage device of the X-ray detection module.

The transmitting may include: selecting at least one X-ray detection module from among the plurality of X-ray detection modules; and transmitting the acquired X-ray data to the selected X-ray detection module.

The selecting may include: grouping the plurality of X-ray detection modules into a plurality of groups; and selecting at least one group from among the plurality of groups. The transmitting may include transmitting the acquired X-ray data to the selected at least one group.

The selecting may include: grouping the plurality of X-ray detection modules into a plurality of groups, based on an external input; and selecting at least one group from among the plurality of groups. The transmitting may include transmitting the acquired X-ray data to the selected at least one group.

The selecting may include: randomly grouping the plurality of X-ray detection modules into a plurality of groups; and selecting at least one group from among the plurality of groups. The transmitting may include transmitting the acquired X-ray data to the selected at least one group.

The method may further include storing all or some of the acquired X-ray data in a storage device of the at least one other X-ray detection module.

The method may further include outputting the acquired X-ray data to at least one of the activated X-ray detection module and the at least one other X-ray detection module.

According to one or more exemplary embodiments, an apparatus for storing all or some of X-ray data of an object, acquired from at least one of a plurality of mutually communicable X-ray detection modules, in the plurality of X-ray detection modules, includes: a data processor that acquires the X-ray data by using an X-ray detection module; and a transmitter that transmits all or some of the acquired X-ray data to at least one other X-ray detection module other than the X-ray detection module.

The apparatus may further include an activator that activates at least one of the plurality of X-ray detection modules, wherein, the data processor may acquire the X-ray data by using the activated X-ray detection module, and the transmitter may transmit all or some of the acquired X-ray data to at least one other X-ray detection module other than the activated X-ray detection module.

The activator may activate at least one X-ray detection module included in a predetermined X-ray-detectable range among the plurality of X-ray detection modules depending on a size of the object.

The data processor may allow a storage device of the X-ray detection module to store the acquired X-ray data.

The transmitter may include a selector that selects at least one X-ray detection module from among the plurality of X-ray detection modules, and the transmitter may transmit the acquired X-ray data to the selected X-ray detection module.

The selector may group the plurality of X-ray detection modules into a plurality of groups, and selects at least one group from among the plurality of groups. The transmitter may transmit the acquired X-ray data to the selected at least one group.

The selector may group the plurality of X-ray detection modules into a plurality of groups, based on an external input, and selects at least one group from among the plurality of groups. The transmitter may transmit the acquired X-ray data to the selected at least one group.

The selector may randomly group the plurality of X-ray detection modules into a plurality of groups, and select at least one group from among the plurality of groups. The transmitter may transmit the acquired X-ray data to the selected at least one group.

The data processor may allow a storage device of the at least one other X-ray detection module to store all or some of the acquired X-ray data.

The apparatus may further include an output device that outputs the acquired X-ray data to at least one of the activated X-ray detection module and the at least one other X-ray detection module.

According to one or more exemplary embodiments, there is provided is a non-transitory computer-readable storage medium storing a program for executing the method in a computer.

BRIEF DESCRIPTION OF THE DRAWINGS

The above and/or other aspects will become more apparent by describing certain exemplary embodiments, with reference to the accompanying drawings, in which:

FIGS. 6A, 6B, and 6C are diagrams for describing a method of transmitting X-ray data to X-ray detection module groups, according to an exemplary embodiment;

DETAILED DESCRIPTION

Figure 1:
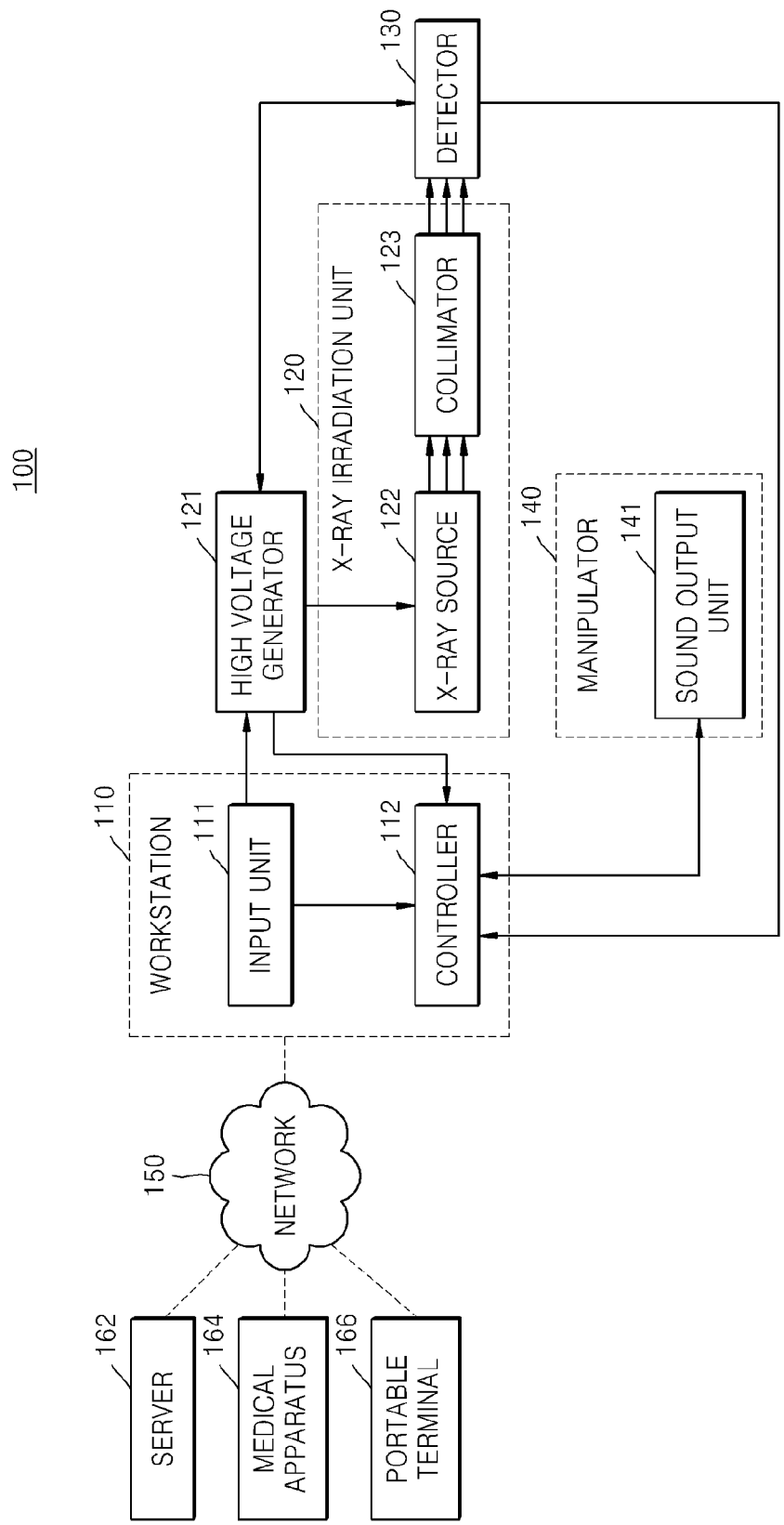
FIG. 1 is a diagram illustrating a configuration of an X-ray apparatus, according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms is described in detail. Thus, the terms used herein have to be defined based on the meaning of the terms together with the description throughout the specification.

When a part "includes" or "comprises" an element, unless there is a particular description contrary thereto, the part can further include other elements, not excluding the other elements. The term 'unit' in the exemplary embodiments means a software component or hardware components such as a field-programmable gate array (FPGA) or an application-specific integrated circuit (ASIC), and performs a specific function. However, the term 'unit' is not limited to software or hardware. The 'unit' may be formed so as to be in an addressable storage medium, or may be formed so as to operate one or more processors. Thus, for example, the term 'unit' may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and 'units' may be associated with the smaller number of components and 'units', or may be divided into additional components and 'units'.

Expressions such as "at least one of," when preceding a list of elements, modify the entire list of elements and do not modify the individual elements of the list.

Throughout the specification, an "image" may mean multi-dimensional data formed of discrete image elements (e.g., pixels in a two-dimensional (2D) image and voxels in a three-dimensional (3D) image). For example, the image may include a medical image of an object which is captured by a computed tomography (CT) image-capturing apparatus.

Throughout the specification, an "object" may include a human, an animal, or a part of a human or animal. For example, the object may include organs such as liver, heart, womb, brain, breast, abdomen, or the like, or a blood vessel. The object may include a phantom. The phantom means a material having a volume that is very close to a density and effective atomic number of an organism, and may include a sphere phantom having a characteristic similar to a physical body.

Throughout the specification, a "user" may be, but is not limited to, a medical expert including a doctor, a nurse, a medical laboratory technologist, a medial image expert, and a technician who repairs a medical apparatus.

FIG. 1 is a block diagram of an X-ray apparatus 100. The X-ray apparatus 100 shown in FIG. 1 may be a stationary X-ray apparatus or a mobile X-ray apparatus.

Referring to FIG. 1, the X-ray apparatus 100 includes a workstation 110, an X-ray irradiation unit 120, a high voltage generator 121, and a detector 130.

The workstation 110 includes an input unit 111 through which a user may input commands for manipulating the X-ray apparatus 100 including manipulating an X-ray irradiation, and a controller 112 controlling operations of the X-ray apparatus 100.

The high voltage generator 121 generates a high voltage for generating X-rays, and applies the high voltage to an X-ray source 122.

The X-ray irradiation unit 120 includes the X-ray source 122 receiving the high voltage applied from the high voltage generator 121 to generate and irradiate the X-ray, and a collimator 123 for guiding a path of the X-ray irradiated from the X-ray source 122.

The detector 130 detects the X-ray that is irradiated from the X-ray irradiation unit 120 and has transmitted through the object. The detector 130 may include a plurality of detection modules.

The detector 130 may be referred to as an X-ray detector. An X-ray detector may be a direct conversion detector and an indirect conversion detector depending on a method of converting an X-ray to an electrical signal. The direct conversion detector may use a semiconductor compound that directly generates an electrical signal by absorbing an X-ray without undergoing an intermediate stage. When an X-ray is irradiated, a carrier including an electron-hole pair may be temporarily generated in the semiconductor compound. In the carrier including the electron-hole pair, due to an electric field that is applied to both ends of a material, an electron may move to a positive pole, and a positive hole may move to a negative pole. In the indirect conversion detector, an X-ray passing through an object reacts with a scintillator to emit a photon having a wavelength of a visible light region, and a photodiode receives the photon to convert the photon into an electrical signal, which is transferred to an external personal computer (PC) through a data acquisition system (DAS). In the indirect conversion detector, an analog signal output from a photodiode is converted into a digital signal by an analog-to-digital converter (DAC) of the DAS, and thus, digital data is transmitted. The detector 130 may use a function of a memory equipped in the ADC without including a separate memory.

A performance of a related art X-ray detector is limited in detecting a high-resolution image, and despite an additional storage device not being equipped in a detection module, it is not difficult to transmit data. However, a pixel size is further reduced (for example, to 500 um or less), and thus, when continuously capturing high-resolution images, it is difficult to obtain a clear image by using only a related art detector.

The X-ray apparatus 100 may further include a manipulator 140 including a sound output unit 141 outputting sound representing information relating to imaging operation such as the X-ray irradiation under a control of the controller 112.

The workstation 110, the X-ray irradiation unit 120, the high voltage generator 121, and the detector 130 may be connected to each other via wires or wirelessly. If they are connected to each other wirelessly, a device (not shown) for synchronizing clocks with each other may be further included.

The input unit 111 may include a keyboard, a mouse, a touch screen, a voice recognizer, a fingerprint recognizer, an iris recognizer, and the like. The user may input a command for irradiating the X-ray via the input unit 111, which may include a switch for inputting the command. The switch may be configured so that an irradiation command for irradiating the X-ray may be input only when the switch is pushed twice.

That is, when the user pushes the switch, a prepare command for performing a pre-heating operation for X-ray irradiation may be input through the switch, and then, when the user pushes the switch once more, the irradiation command for irradiating the X-ray may be input through the switch. When the user manipulates the switch as described above, the input unit 111 generates signals corresponding to the commands input through the switch manipulation, that is, a prepare signal and an irradiation signal, and outputs the generated signals to the high voltage generator 121 generating a high voltage for generating the X-ray.

When the high voltage generator 121 receives the prepare signal output from the input unit 111, the high voltage generator 121 starts a pre-heating operation, and when the pre-heating is finished, the high voltage generator 121 outputs a ready signal to the controller 121. The detector 130 also needs to prepare for detecting the X-ray, and thus, when the high voltage generator 121 receives the prepare signal output from the input unit 111, the high voltage generator 121 outputs a prepare signal to the detector 130 at the same time of performing the pre-heating operation, so that the detector 130 may prepare for detecting the X-ray transmitted through the object. The detector 130 prepares for detecting the X-ray when receiving the prepare signal, and when the preparing for the detection is finished, the detector 130 outputs a ready signal to the high voltage generator 121 and the controller 112.

When the pre-heating operation of the high voltage generator 121 is finished, the detector 130 is ready for the detecting the X-ray, and the irradiation signal is output from the input unit 111 to the high voltage generator 121, the high voltage generator 121 generates and applies the high voltage to the X-ray source 122, and the X-ray source 122 irradiates the X-ray.

When the irradiation signal is output from the input unit 111, the controller 112 may output a sound output signal to the sound output unit 141 so that the sound output unit 141 outputs predetermined sound and the object may recognize the irradiation of X-ray. The sound output unit 141 may output sound representing other information relating to the imaging, in addition to the X-ray irradiation. In FIG. 1, the sound output unit 141 is included in the manipulator 140; however, the exemplary embodiments are not limited thereto, and the sound output unit 141 may be located at a different location from the manipulator 140. For example, the sound output unit 141 may be included in the workstation 110, or may be located on a wall surface of an examination room in which the X-ray imaging of the object is performed.

The controller 112 controls locations of the X-ray irradiation unit 120 and the detector 130, imaging timing, and imaging conditions according to imaging conditions set by the user.

In detail, the controller 112 controls the high voltage generator 121 and the detector 130 according to the command input via the input unit 111 so as to control an irradiation timing of the X-ray, an intensity of the X-ray, and an irradiation region of the X-ray. The controller 112 adjusts the location of the detector 130 according to a predetermined imaging condition, and controls an operation timing of the detector 130.

The controller 112 generates a medical image of the object by using image data transmitted from the detector 130. In particular, the controller 121 receives the image data from the detector 130, and then, generates the medical image of the object by removing noise in the image data, and adjusting a dynamic range and interleaving of the image data.

The X-ray apparatus 100 shown in FIG. 1 may further include an output device (not shown) for outputting the medical image generated by the controller 112. The output device may output information that is needed for the user to manipulate the X-ray apparatus 100, for example, a user interface (UI), user information, or object information. The output device may include a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a three-dimensional (3D) display, a transparent display, and other various output devices.

The workstation 110 shown in FIG. 1 may further include a communicator (not shown) that may be connected to a server 162, a medical apparatus 164, and a portable terminal 166 via a network 150.

The communicator may be connected to the network 150 via wires or wirelessly to communicate with the external server 162, the external medical apparatus 164, or the external portable terminal 166. The communicator may transmit or receive data relating to diagnosis of the object via the network 150, and may transmit or receive medical images captured by the medical apparatus 164, for example, a CT, an MRI, or an X-ray apparatus. The communicator may receive medical history or treatment schedule of an object (e.g., a patient) from the server 162 to diagnose the object. The communicator may perform data communication with the portable terminal 166 such as a mobile phone of a doctor or a patient, a personal digital assistant (PDA), or a laptop computer, as well as the server 162 or the medical apparatus 164 in a hospital.

The communicator may include one or more elements enabling to communicate with external apparatuses, for example, a short distance communication module, a wired communication module, and a wireless communication module.

The short distance communication module is a module for communicating with a device located within a predetermined distance. The short distance communication technology may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, the exemplary embodiments are not limited thereto.

The wired communication module is a module for communicating by using an electric signal or an optical signal, and the wired communication technology may be wired communication technology using a pair cable, a coaxial cable, or an optical fiber cable.

The wireless communication module may transmit and receive a wireless signal to and from at least one of a base, an external device, and a server in a mobile communication network. The wireless signal may be a voice call signal, a video call signal, or various types of data according to text and multimedia messages transmission.

The X-ray apparatus 100 shown in FIG. 1 may include a plurality of digital signal processors (DSPs), an ultra-small calculator, and a processing circuit for specialized usage (for example, a high speed analog to digital (A/D) conversion, a high speed Fourier transformation, an array process, etc.).

The communication between the workstation 110 and the X-ray generator 120, the workstation 110 and the high voltage generator 211, and the workstation 110 and the detector 130 may use a high speed digital interface, such as low voltage differential signaling (LVDS), asynchronous serial communication, such as universal asynchronous receiver transmitter (UART), synchronous serial communication, or a low latency network protocol, such as a controller area network (CAN), and other various communication methods.

Figure 7:
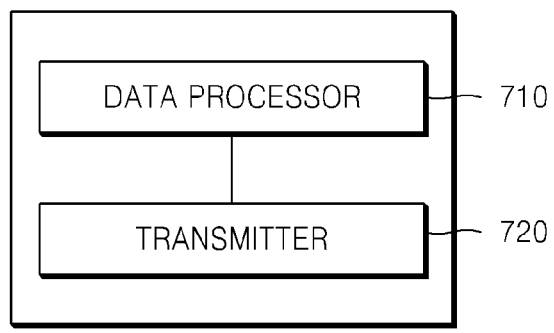
FIG. 7 is a block diagram illustrating an apparatus for storing X-ray data in an X-ray detection module, according to an exemplary embodiment.

FIG. 7 is a block diagram illustrating an apparatus 700 for storing X-ray data in at least one X-ray detection module, according to an exemplary embodiment.

The apparatus 700 according to an exemplary embodiment may include a data processor 710 and a transmitter 720.

The data processor 710 may acquire the X-ray data by using an X-ray detection module. The data processor 710 may allow the storage device of at least one other X-ray detection module to store all or some of the acquired X-ray data. The data processor 710 may allow the storage device of the X-ray detection module to store the acquired X-ray data. The storage device may include at least one storage medium including at least one of a flash memory, a hard disk, a multimedia micro card, a card type memory (a secure digital (SD) card, an extreme digital (XD) card, or the like), a random access memory (RAM), a static random access memory (SRAM), a read-only memory (ROM), an electrically erasable programmable read-only memory (EEPROM), and a programmable read-only memory (PROM). The apparatus 700 may use a web storage or a cloud server which performs a storage function of the storage device on the Web.

Operations of the components 710 and 720 of the apparatus 700 illustrated in FIG. 7 are described below in more detail with reference to FIG. 2.

Figure 2:
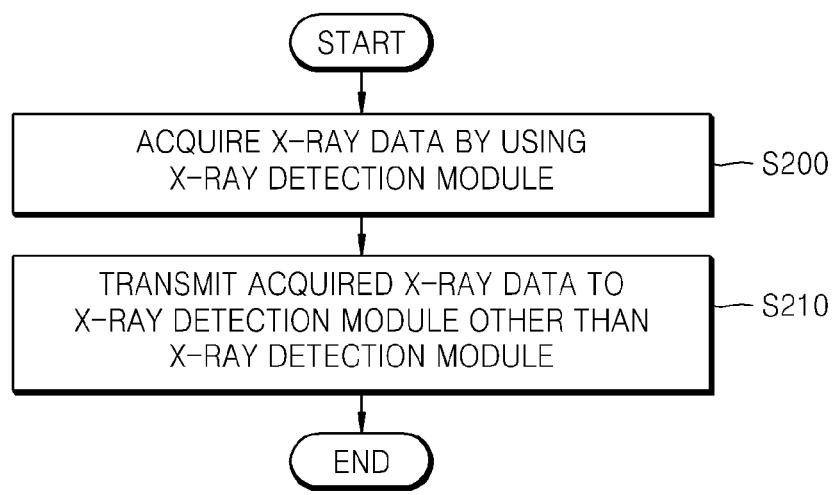
FIG. 2 is a flowchart illustrating a method of storing X-ray data in at least one X-ray detection module, according to an exemplary embodiment.

FIG. 2 is a flowchart illustrating a method of storing X-ray data in at least one X-ray detection module, according to an exemplary embodiment.

In operation S200, the data processor 710 may acquire X-ray data by using an X-ray detection module, i.e., a first X-ray detection module. The X-ray data may include information of an object which is acquired from an X-ray passing through the object.

At least one X-ray detection module according to an exemplary embodiment may include at least one storage device. The data processor 710 may store all or some of acquired X-ray data in the storage device of the first X-ray detection module.

In operation S210, the transmitter 720 may transmit all or some of the acquired X-ray data to at least one other X-ray detection module other than the X-ray detection module, i.e., a second X-ray detection module. The storage device may be controlled by a storage device controller included in the respective X-ray detection modules. That is, the storage device controller may store all or some of X-ray data, received from the first X-ray detection module, in a storage device of at least one other X-ray detection module other than the first X-ray detection module.

Figure 8:
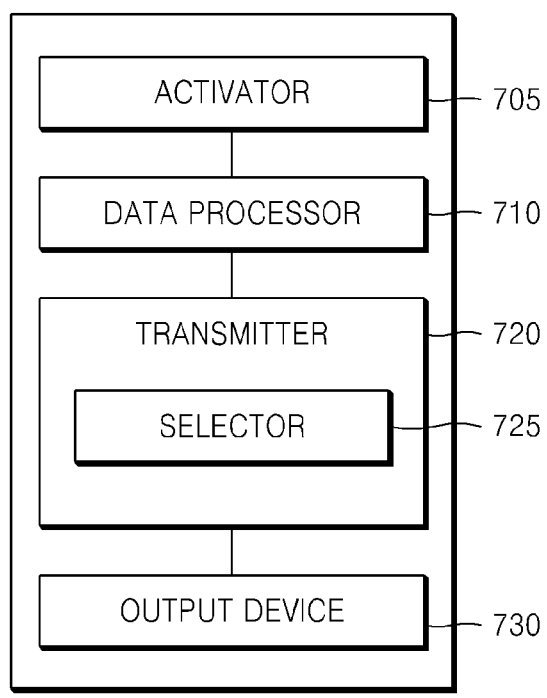
FIG. 8 is a block diagram illustrating an apparatus for storing X-ray data in an X-ray detection module, according to an exemplary embodiment.

FIG. 8 is a block diagram illustrating an apparatus 700 for storing X-ray data in at least one X-ray detection module, according to an exemplary embodiment. The apparatus 700 for storing X-ray data in at least one X-ray detection module, according to an exemplary embodiment, may include the activator 705, a data processor 710, a transmitter 720, a selector 725, and an output device 730. The data processor 710 and the transmitter 720 are described above with reference to FIG. 7.

An X-ray detector according to an exemplary embodiment may include a plurality of X-ray detection modules. The X-ray detection modules may communicate with each other. The activator 705 of the apparatus 700 may activate all or some of the plurality of X-ray detection modules to receive X-ray data. For example, only one of the plurality of X-ray detection modules may be activated to receive the X-ray data. The activator 705 may deactivate some of the plurality of X-ray detection modules so as not to receive X-ray data. The activator 705 may activate at least one X-ray detection module included in a predetermined X-ray-detectable range among the plurality of X-ray detection modules depending on a size of an object. A scout view may be used for determining the size of the object before irradiating an X-ray onto the object. The scout view may include a pre-acquired digital projection phase used to determine a position which is to be imaged, for accurately imaging a horizontal cross-sectional surface of a desired part in X-ray imaging.

The activator 705 may measure the size of the object by using the scout view, and predetermine a range, in which an X-ray passing through the object is detected, by using the size of the object, a distance and angle between the object and an X-ray generator, and a distance and angle between the object and an X-ray detection module.

The data processor 710 may acquire the X-ray data by using an activated X-ray detection module. The data processor 710 may allow the storage device of at least one other X-ray detection module to store all or some of the acquired X-ray data. The data processor 710 may allow the storage device of the activated X-ray detection module to store the acquired X-ray data.

The transmitter 720 may transmit all or some of the acquired X-ray data to at least one other X-ray detection module other than the activated X-ray detection module, based on a selection by the selector 725. The selector 725 may select at least one X-ray detection module adjacent or not adjacent to the activated X-ray detection module.

As another example, the selector 725 may group the X-ray detection modules into groups and select a group to which all or some of the acquired X-ray data may be transmitted. For example, a selection of the group may be performed based on an external input. As another example, the selector 725 may randomly group the X-ray detection modules into the groups, and select a group from the random groups to which all or some of the acquired X-ray data may be transmitted.

The output device 730 may allow the acquired X-ray data to be output from at least one of the activated X-ray detection module and another X-ray detection module. The output device 730 may output the X-ray data to display the X-ray data in a display. The output device 730 may include a printer, a CRT display, an LCD, a PDP, an OLED display, a FED, an LED display, a VFD, a DLP display, a PFD, a 3D display, a transparent display, etc., and include various output devices within a scope obvious to those skilled in the art. The output device 730 may output the X-ray data to store the X-ray data in an external storage device.

Figure 3A:
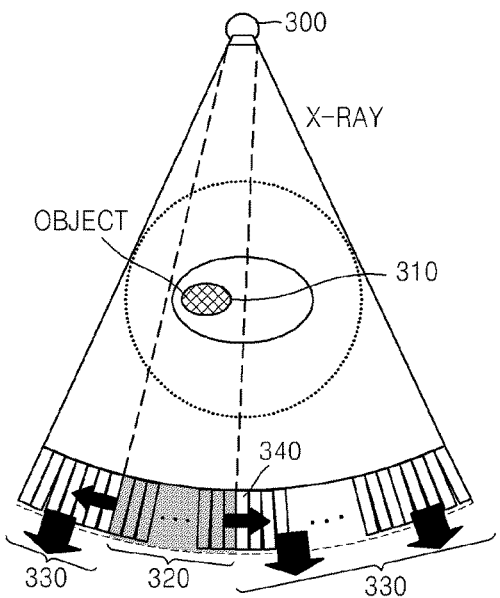
FIGS. 3A and 3B are diagrams for describing a method of storing X-ray data in an X-ray detection module, according to an exemplary embodiment.
Figure 3B:
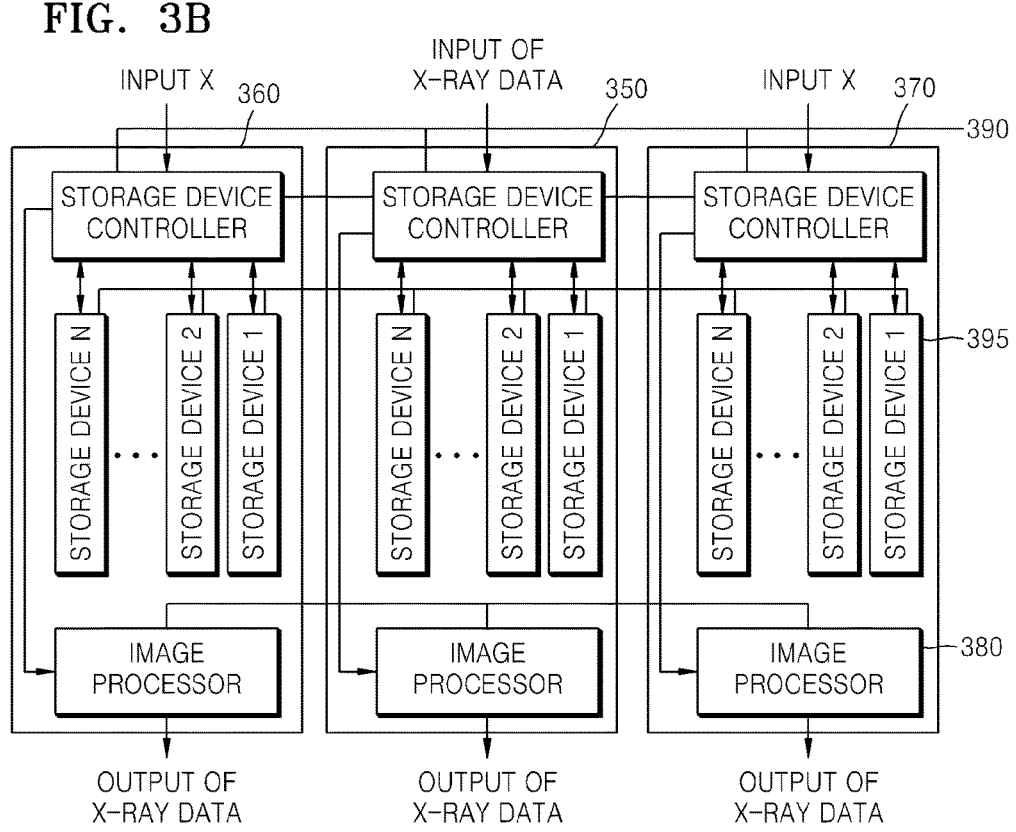

FIGS. 3A and 3B are diagrams for describing a method of storing X-ray data in at least one X-ray detection module, according to an exemplary embodiment.

Referring to FIG. 3A, an X-ray generator 300 may be an apparatus that generates an X-ray. When the X-ray generator 300 generates an X-ray, the X-ray may be irradiated in a certain range. According to an exemplary embodiment, a size of an object 310 may be previously determined by using a scout view. An activator 705 may determine an X-ray-detectable range based on a size of an object by using the scout view as described above. The activator 705 may activate at least one X-ray detection module 320 included in the X-ray-detectable range among a plurality of the X-ray detection modules. X-ray data may be acquired by the activated X-ray detection module 320. As described above, X-ray data may be acquired by only the activated X-ray detection module 320 which is included in the X-ray-detectable range in which an X-ray passing through an object is to be detected. In other words, a deactivated X-ray detection module 330 cannot acquire X-ray data. The activated X-ray detection module 320 may transmit the X-ray data to the deactivated X-ray detection module 330.

Referring to FIG. 3B, each of first, second, and third X-ray detection modules 350, 360 and 370 may include at least one or more image processors 380, which process input data, and at least one or more storage devices 395. Each of the first to third X-ray detection modules 350, 360 and 370 may include a storage device controller 390 that controls a storage device 395.

The first X-ray detection module 350 may be an activated X-ray detection module, and each of the second and third X-ray detection modules 360 and 370 may be a deactivated X-ray detection module. Referring to FIG. 3B, since the first X-ray detection module 350 is the activated X-ray detection module, the first X-ray detection module 350 may receive X-ray data. Since each of the second and third X-ray detection modules 360 and 370 is the deactivated X-ray detection module, each of the second and third X-ray detection modules 360 and 370 does not receive X-ray data. The first X-ray detection module 350 may transmit the received X-ray data to its storage device controller 390.

The first X-ray detection module 350 may store all or some of the received X-ray data in the storage device 395 included in the first X-ray detection module 350, according to a control of the storage device controller 390. Also, all or some of X-ray data acquired by the first X-ray detection module 350 may be transmitted to the second X-ray detection module 360 or the third X-ray detection module 370 according to a data transmission command applied from the transmitter 720 of the apparatus 700 to the storage device controller 390 of the first X-ray detection module 350. The second or third X-ray detection module 360 or 370 including the storage device may store the received X-ray data in the storage device. The received X-ray data may be stored according to a control of the respective storage device controller 390 included in each of the second and third X-ray detection modules 360 and 370. The storage device controller 390 may transmit the received X-ray data to the image processor 380. The image processor 380 may convert the transmitted X-ray data into data of an image of an object, and output the converted data.

Figure 4:
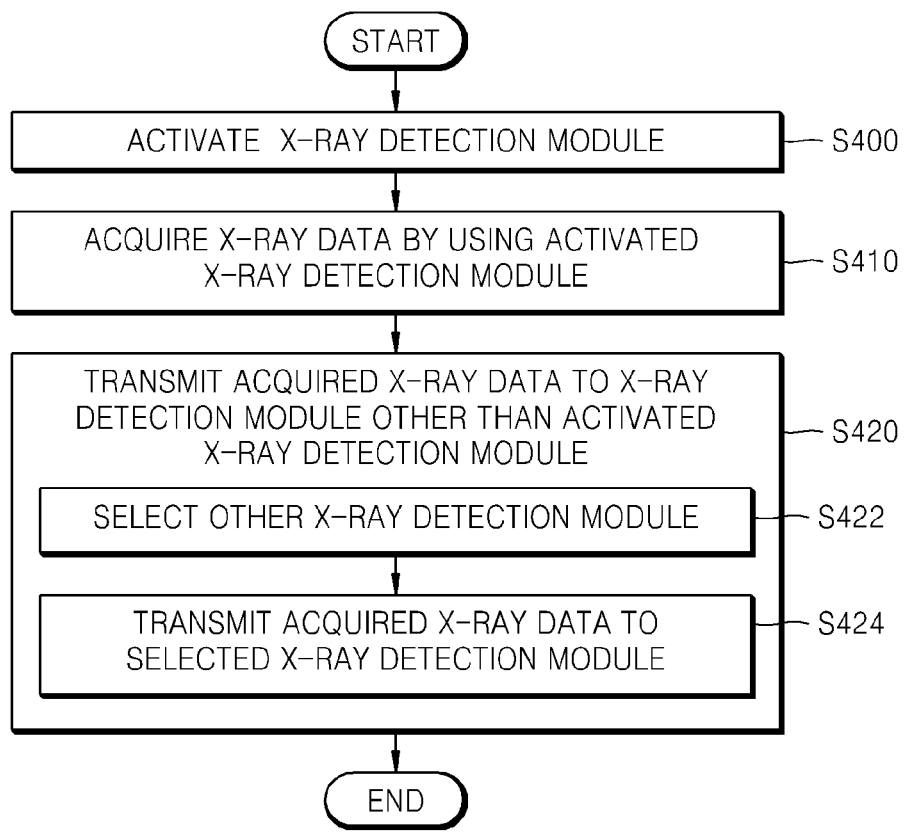
FIG. 4 is a flowchart illustrating a method of storing X-ray data in an X-ray detection module, according to an exemplary embodiment.

FIG. 4 is a flowchart illustrating a method of storing X-ray data in at least one X-ray detection module, according to an exemplary embodiment. Operations of FIG. 4 are described with reference to FIG. 8.

In operation S400, at least one of a plurality of X-ray detection modules may be activated by the activator 705 of the apparatus 700 according to an exemplary embodiment.

In operation S410, the data processor 710 may acquire the X-ray data by using an activated X-ray detection module. The X-ray data may include information of the object which is acquired from the X-ray passing through the object.

As described above, each of the X-ray detection modules according to an exemplary embodiment may be separately activated, and the X-ray data of the object may be acquired by using an activated X-ray detection module among the plurality of X-ray detection modules. In other words, the X-ray data may be acquired by using only the activated X-ray detection module. Each X-ray detection module according to an exemplary embodiment may include at least one storage device. The data processor 710 may store all or some of the acquired X-ray data in the storage device of the activated X-ray detection module.

According to an exemplary embodiment, transmission operation S420 may include operation S422 of selecting at least one X-ray detection module from among the plurality of X-ray detection modules and operation S424 of transmitting acquired X-ray data to the selected X-ray detection module.

In operation S422, the selector 725 may select at least one X-ray detection module from among the plurality of X-ray detection modules. When the selector 725 selects at least one X-ray detection module from among the plurality of X-ray detection modules, the selector 725 may select at least one X-ray detection module adjacent to an activated X-ray detection module. The selector 725 may group the plurality of X-ray detection modules into a plurality of groups, and select at least one group from among the plurality of groups. When the size of the object is large, the selector 725 may group a plurality of X-ray detection modules. When the size of the object is large, the selector 725 may group a plurality of activated X-ray detection modules, and group a plurality of deactivated X-ray detection modules, thereby efficiently transmitting or storing X-ray data.

In operation S424, the transmitter 720 may transmit the acquired X-ray data to the selected X-ray detection module. The transmitter 720 may group the plurality of X-ray detection modules into a plurality of groups on the basis of an external input, select at least one group from among the plurality of groups, and transmit the acquired X-ray data to the selected at least one group. The external input may include a user input, which is received by an external input receiving unit, for grouping at least one X-ray detection module. For example, the external input may include an input of information about a group which is to be grouped by a user. For example, the external input may include an input for grouping an X-ray detection module in which a residual space of the storage device exceeds a predetermined reference. The input may be an input for grouping at least one X-ray detection module in which the residual space of the storage device exceeds about 50%.

When a space of the storage device of the activated X-ray detection module is insufficient, the transmitter 720 may transmit the X-ray data to another X-ray detection module. The space of the storage device being insufficient denotes a residual space of the storage device being about 0% or about 10%, and the residual space may be previously set by the user. The transmitter 720 may transmit the acquired X-ray data to an X-ray detection module, in which the most space of the storage device remains, among the other X-ray detection modules.

The output device 730 may output the X-ray data obtained from at least one of the activated X-ray detection module and the other X-ray detection modules. The output device 730 may include an X-ray image display apparatus.

Figure 5A:
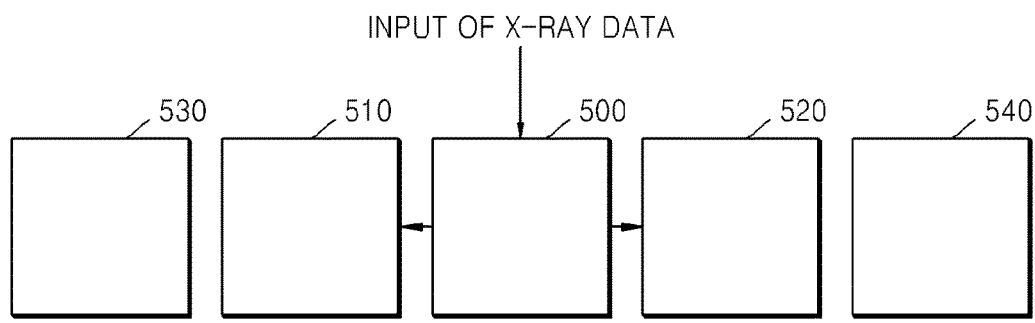
FIGS. 5A, 5B and 5C are diagrams for describing a method of transmitting X-ray data to X-ray detection modules, according to an exemplary embodiment.
Figure 5B:
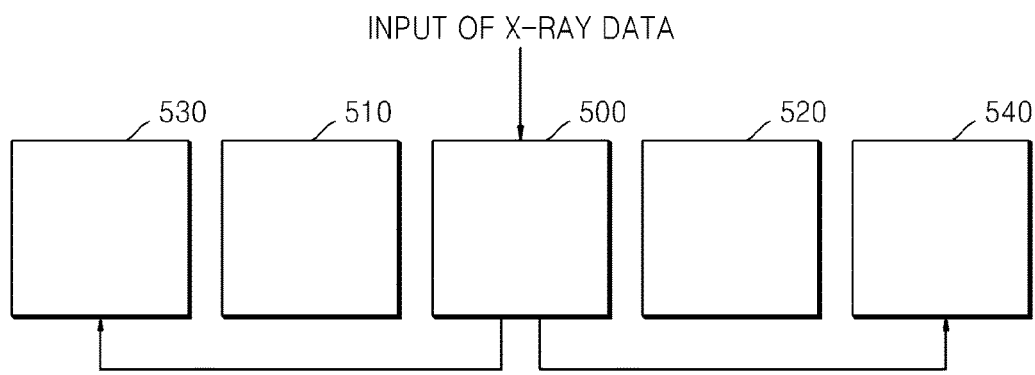
Figure 5C:
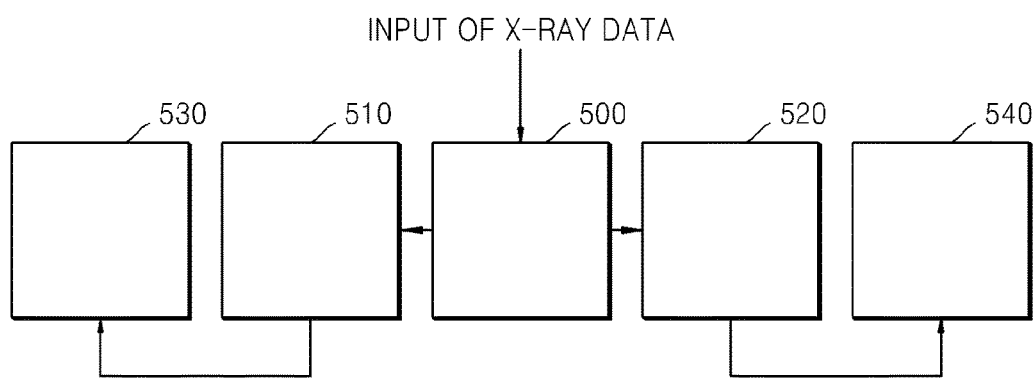

FIGS. 5A to 5C are diagrams for describing a method of transmitting X-ray data to a plurality of X-ray detection modules, according to an exemplary embodiment. In FIGS. 5A to 5C, a block 500 may correspond to the first X-ray detection module 350 of FIG. 3B. A block 510 may correspond to the second X-ray detection module 360 of FIG. 3B, and a block 520 may correspond to the third X-ray detection module 370 of FIG. 3B. A block 530 may be a fourth X-ray detection module, and a block 540 may be a fifth X-ray detection module.

Referring to FIG. 5A, the first X-ray detection module 500 may receive X-ray data, and transmit the acquired X-ray data to the second and/or third X-ray detection module 510 or 520.

Referring to FIG. 5B, the first X-ray detection module 500 may receive the X-ray data, and transmit the acquired X-ray data to the fourth and/or fifth X-ray detection module 530 and 540.

Referring to FIG. 5C, the first X-ray detection module 500 may receive X-ray data. The second X-ray detection module 510 may transmit the X-ray data, received from the first X-ray detection module 500, to the fourth X-ray detection module 530. The third X-ray detection module 520 may transmit the X-ray data, received from the first X-ray detection module 500, to the fifth X-ray detection module 540. Each X-ray detection module may transmit received X-ray data to at least one X-ray detection module other than an X-ray detection module that has received the X-ray data.

Figure 6A:
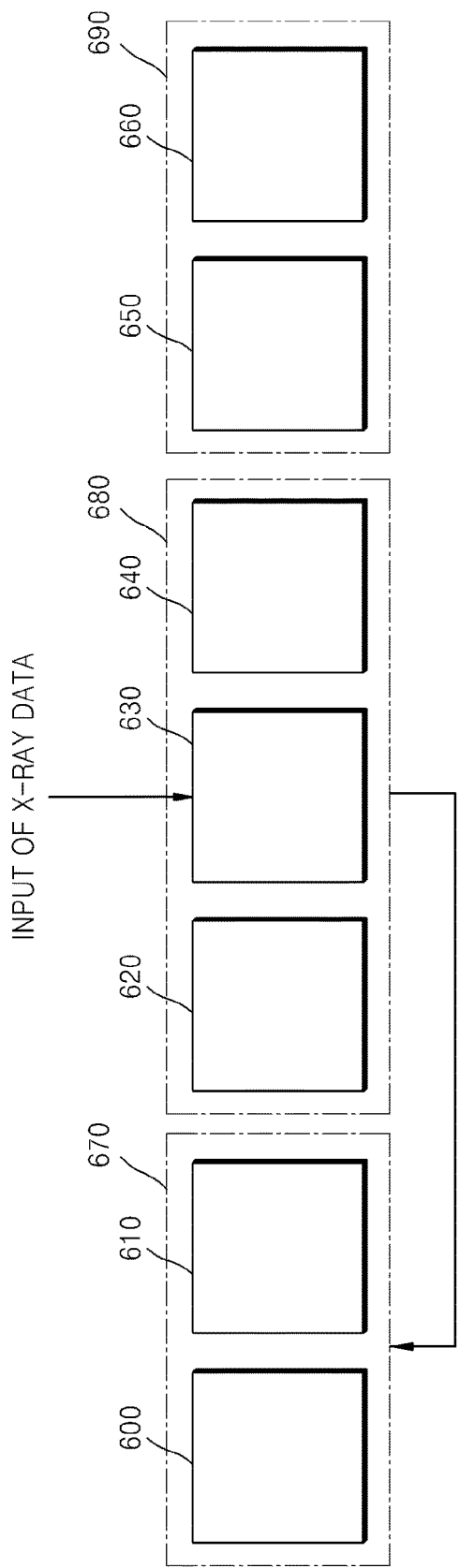
Figure 6B:
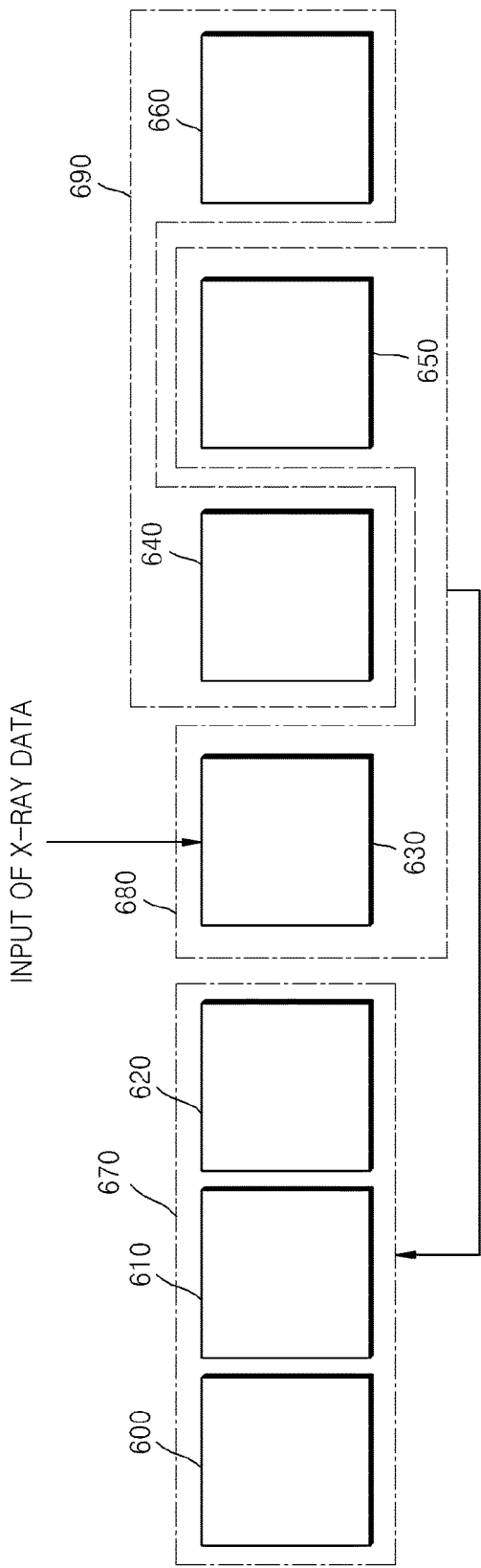

FIGS. 6A to 6C are diagrams for describing a method of transmitting X-ray data to each X-ray detection module group, according to an exemplary embodiment. In FIGS. 6A to 6C, a plurality of square blocks 600 to 660 respectively are the above-described X-ray detection modules. In the following description, for convenience, it is assumed that the square blocks 600 to 660 respectively are first to seventh X-ray detection modules 600 to 660.

The selector 725 may group a plurality of X-ray detection modules into a plurality of groups. The selector 725 may group the plurality of X-ray detection modules into the plurality of groups on the basis of an external input.

Referring to FIG. 6A, the selector 725 may group the first and second X-ray detection modules 600 and 610 into a first group 670, the third, fourth, and fifth X-ray detection modules 620, 630, and 640 into a second group 680, and the sixth and seventh X-ray detection modules 650 and 660 into a third group 690.

For example, the selector 725 may group a plurality of X-ray detection modules according to a user input. The selector 725 may group a plurality of X-ray detection modules that are not adjacent to each other.

Referring to FIG. 6B, the selector 725 may group the first to third X-ray detection modules 600, 610, and 620 into the first group 670, group the fourth and sixth X-ray detection modules 630 and 650 into the second group 680, and group the fifth and seventh X-ray detection modules 640 and 660 into the third group 690.

Referring to FIG. 6C, the selector 725 may randomly group a plurality of X-ray detection modules into a plurality of groups. For example, the selector 725 may randomly group the first and third X-ray detection modules 600 and 620 into the first group 670, the second, fourth and sixth X-ray detection modules 610, 630 and 650 into the second group 680, and the fifth and seventh X-ray detection modules 640 and 660 into the third group 690.

The transmitter 720 may transmit or receive the X-ray data between groups.

Referring to FIGS. 6A, 6B, and 6C, the X-ray data may be input to the fourth X-ray detection module 630 included in the second group 680, and the fourth X-ray detection module 630 may transmit the input X-ray data to the first group 670 and/or the third group 690.

The above-described exemplary embodiments may be written as computer programs and may be implemented in computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.), and transmission media such as Internet transmission media.

It should be understood that the exemplary embodiments described therein should be considered in a descriptive sense only and not for purposes of limitation. Descriptions of features or aspects within each exemplary embodiment should be considered as available for other similar features or aspects in other exemplary embodiments.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A method of storing X-ray data of an object, acquired from mutually communicable X-ray detection modules, the method comprising:
   acquiring the X-ray data by using an X-ray detection module of the X-ray detection modules;
   transmitting all or some of the acquired X-ray data to other X-ray detection module, of the X-ray detection modules, that is different from the X-ray detection module that has acquired the X-ray data; and
   storing the all or some of the acquired X-ray data in a storage device of the other X-ray detection module.

2. The method of claim 1, further comprising:
   activating the X-ray detection module,
   wherein the acquiring comprises acquiring the X-ray data by using the activated X-ray detection module, and
   the transmitting comprises transmitting the all or some of the acquired X-ray data to the other X-ray detection module which is an X-ray detection module different from the activated X-ray detection module.

3. The method of claim 2, wherein the activating comprises:
   activating the X-ray detection module which is included in a predetermined X-ray-detectable range depending on a size of the object.

4. The method of claim 2, wherein the activating comprises storing some of the acquired X-ray data in a storage device of the activated X-ray detection module.

5. The method of claim 1, wherein the transmitting comprises:
   selecting the other X-ray detection module from the X-ray detection modules; and
   transmitting the some or all of the acquired X-ray data to the other X-ray detection module, based on the selecting.

6. The method of claim 1, further comprising:
   grouping the X-ray detection modules into a plurality of groups, prior to the transmitting; and
   selecting a group, from the plurality of groups, that does not include the X-ray detection module that has acquired the X-ray data,
   wherein the transmitting comprises transmitting the acquired X-ray data to the selected group, the selected group including the other X-ray detection module.

7. The method of claim 1, further comprising:
   grouping the X-ray detection modules into a plurality of groups, prior to the transmitting, based on an external input; and
   selecting a group from the plurality of groups, that does not include the X-ray detection module that has acquired the X-ray data,
   wherein the transmitting comprises transmitting the all or some of the acquired X-ray data to the selected group, the selected group including the other X-ray detection module.

8. The method of claim 1, further comprising:
   randomly grouping the X-ray detection modules into a plurality of groups, prior to the transmitting; and
   selecting a group, from the plurality of groups, that does not include the X-ray detection module that has acquired the X-ray data,
   wherein the transmitting comprises transmitting the all or some of the acquired X-ray data to the selected group, the selected group including the other X-ray detection module.

9. The method of claim 2, further comprising:
   outputting the acquired X-ray data from at least one among the activated X-ray detection module and the other X-ray detection module.

10. An apparatus for storing X-ray data of an object, acquired from mutually communicable X-ray detection modules, the apparatus comprising:
    a processor configured to acquire the X-ray data by using an X-ray detection module, of the X-ray detection modules, transmit all or some of the acquired X-ray data to other X-ray detection module, of the X-ray detection modules, that is different from the X-ray detection module that has acquired the X-ray data, and store the all or some of the acquired X-ray data in a storage device of the other X-ray detection module.

11. The apparatus of claim 10, wherein the processor is configured to activate the X-ray detection module, prior to X-ray data acquisition, acquire the X-ray data by using the activated X-ray detection module, and transmit the all or some of the acquired X-ray data to the other X-ray detection module which is an X-ray module different from the activated X-ray detection module.

12. The apparatus of claim 11, wherein the processor is configured to activate the X-ray detection module included in a predetermined X-ray-detectable range, depending on a size of the object.

13. The apparatus of claim 10, wherein the processor is further configured to store some of the acquired X-ray data in a storage device of the X-ray detection module.

14. The apparatus of claim 10, wherein the processor is configured to select the other X-ray detection module from the X-ray detection modules, and transmit the all or some of the acquired X-ray data to the other X-ray detection module which has been selected.

15. The apparatus of claim 10, wherein the processor is configured to group the X-ray detection modules into a plurality of groups prior to a transmission of the acquired X-ray data, select a group, from the plurality of groups, that does not include the X-ray detection module that has acquired the X-ray data, and transmit the acquired X-ray data to the selected group, the selected group including the other X-ray detection module.

16. The apparatus of claim 10, wherein the processor is configured to group the X-ray detection modules into a plurality of groups prior to a transmission of the acquired X-ray data, based on an external input, select a group from the plurality of groups, that does not include the X-ray detection module that has acquired the X-ray data, and transmit the all or some of the acquired X-ray data to the selected group, the selected group including the other X-ray detection module.

17. The apparatus of claim 10, wherein the processor is configured to randomly group the X-ray detection modules into a plurality of groups prior to a transmission of the acquired X-ray data, select a group from the plurality of groups, that does not include the X-ray detection module that has acquired the X-ray data, and transmit the all or some of the acquired X-ray data to the selected group, the selected group including the other X-ray detection module.

18. The apparatus of claim 11, further comprising:
an output device configured to output the acquired X-ray data from at least one among the activated X-ray detection module and the other X-ray detection module.

* * * * *